United States Patent [19]

Wissner et al.

[11] Patent Number: 4,897,385

[45] Date of Patent: * Jan. 30, 1990

[54] ANTIHYPERTENSIVE PHOSPHATE DERIVATIVES

[75] Inventors: Allan Wissner, Ardsley; Phaik-Eng Sum, New City, both of N.Y.

[73] Assignee: American Cyanamid Company, Stamford, Conn.

[*] Notice: The portion of the term of this patent subsequent to Sep. 29, 2004 has been disclaimed.

[21] Appl. No.: 96,945

[22] Filed: Sep. 15, 1987

Related U.S. Application Data

[63] Continuation of Ser. No. 679,792, Dec. 10, 1984, Pat. No. 4,697,031.

[51] Int. Cl.$^4$ .................. C07F 9/10; A01K 31/685
[52] U.S. Cl. ..................... 514/77; 540/450; 540/542; 546/22; 548/112; 558/169
[58] Field of Search ........... 558/169; 548/112; 546/22; 540/450, 542; 514/77

[56] References Cited

U.S. PATENT DOCUMENTS 4,697,031  9/1987  Wissner et al. ............... 558/169

FOREIGN PATENT DOCUMENTS 0070433  1/1983  European Pat. Off. .

OTHER PUBLICATIONS

Hanahan et al., Biochemical and Biophysical Research Communications, vol. 99, No. 1, 1981, pp. 183–188.
Tence et al., Biochimie, 1981, 63, 723–727.
Tence et al., Biochimica et Biophysica Acta, 755 (1983).

*Primary Examiner*—Anton H. Sutto
*Attorney, Agent, or Firm*—Robert P. Raymond; Edward A. Hedman

[57] ABSTRACT

Antihypertensive phosphate derivatives having the following formula are described:

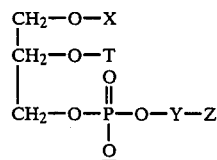

FORMULA 1 wherein X is selected from the group consisting of a phenyl radical substituted at any position with a $C_1$–$C_{20}$ branched or straight chain alkoxy or benzyloxy and optionally substituted at any other positions with one or more groups consisting of $C_1$–$C_{15}$ branched or straight chain alkyl, $C_1$–$C_{15}$ branched or straight chain alkoxy and halogen, and a naphthalene radical substituted at any position with a $C_1$–$C_{20}$ branched or straight chain alkoxy or benzyloxy and optionally substituted at any other positions with one or more groups consisting of $C_1$–$C_{15}$ branched or straight chain alkyl, $C_1$–$C_{15}$ branched or straight chain alkoxy and halogen; T is selected from the group consisting of hydrogen and

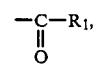

wherein $R_1$ is selected from the group consisting of hydrogen, $C_1C_4$ branched or straight chain alkyl, $C_1$–$C_4$ branched or straight chain alkoxy and $C_1$–$C_4$ branched or straight chain alkylamino; Y is selected from the group of bivalent radicals consisting of —$(CH_2)_p$— and —$(CHR)_p$—, wherein p is an integer from 2 to 10 and the moiety —$(CHR)_p$— represents an alkylene chain substituted with one or more $C_1$–$C_8$ alkyl groups or phenyl groups; Z is selected from the group consisting of

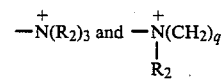

wherein q is an integer from 4–7 and $R_2$ may be the same or different and is selected from the group consisting of hydrogen and $C_1$–$C_4$ branched or straight chain alkyl.

14 Claims, No Drawings

1

ANTIHYPERTENSIVE PHOSPHATE DERIVATIVES

This is a continuation of application Ser. No. 679,792 filed Dec. 10, 1984, now U.S. Pat. No. 4,697,031.

BACKGROUND OF INVENTION

This invention pertains to novel phosphate derivatives, and to methods of preparation of such compounds. This invention is also concerned with compositions useful in the treatment of hypertension.

It is estimated that approximately fifteen percent (15%) or more of the adult population in the United States is hypertensive, i.e., having blood pressures greater than or equal to about 160/95 mm Hg. Of that population, approximately one-half is unaware of their hypertensive condition. An untreated hypertensive is at great risk of developing disabling or fatal left ventricular failure, myocardial infarction, cerebral hemorrhage or infarction, and renal failure at an early age. Hypertension is generally considered the most important risk factor predisposing to coronary and cerebral atherosclerosis. However, it is believed that effective medical control of hypertension will prevent or forestall all complications associated with hypertension, and will prolong the life of the hypertensive patient.

Drug therapy for hypertension includes use of diuretics, sympathetic depressants (e.g., -blockers such as reserpine), vasodilators and finally blockers of sympathetic transmission at the neuroeffector junction (e.g., guanethidine or clonidine).

Among the vasodilators currently employed in hypertension therapy are diazoxide and sodium nitroprusside. Side effects of diazoxide therapy include nausea, vomiting, hyperglycemia and tachycardia. Side effects from sodium nitroprusside therapy include nausea, vomiting, agitation, muscular twitching and cutis anserina if blood pressure is reduced too rapidly. Minoxidil is also often used as a vasodilator in hypertension therapy. However, the side effects of minoxidil include sodium and water retention, and hirsutism. Hydralazine, a mild vasodilator, is also employed. Its side effects include headaches, tachycardia, fluid retention, aggravation of angina, gastrointestinal irritation, lupus-like syndrome, drug fever and psychosis.

Acetyl glyceryl ether phosphocholines have been recognized as having potent biological activity in platelet activation, and in vasoconstriction and vasodilation. See, e.g. U.S. Pat. No. 4,329,302, which issued on May 11, 1982 to Hanahan, et al. Such phosphocholines have been identified as both a platelet activation factor (PAF) and an antihypertensive polar renomedullary lipid (APRL). See R. L. Wykle, et al., FEBS LETTERS, 141: 29-32 (1982); M. L. Blank, et al., BIOCHEMICAL AND BIOPHYSICAL RESEARCH COMMUNICATIONS, 90: 1194-1200 (1979). Antihypertensive phosphocholines do not occur as pre-formed components in the body; rather, such phosphocholines are synthesized by certain cells. See J. Benveniste, et al., INT. ARCHS. ALLERGY APPL. IMMUNN., 66 (Supp. 1): 121-126 (1981); E. E. Muirhead, HYPERTENSION, 2: 444-464 (1980). APRL has been described as being accountable in great measure for the endocrine-type antihypertensive action exerted by the renal medullary and the renomedullary interstitial cells. M. L. Blank, et al., ID.

BRIEF SUMMARY OF THE INVENTION

The phosphate derivatives of this invention are selected from those of the formula 1:

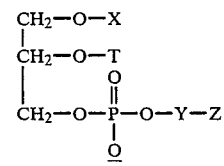

FORMULA 1 wherein X is selected from the group consisting of a phenyl radical substituted at any position with a $C_1$-$C_{20}$ branched or straight chain alkoxy or benzyloxy and optionally substituted at any other positions with one or more groups consisting of $C_1$-$C_{15}$ branched or straight chain alkyl, $C_1$-$C_{15}$ branched or straight chain alkoxy and halogen, and a naphthalene radical substituted at any position with a $C_1$-$C_{20}$ branched or straight chain alkoxy or benzyloxy and optionally substituted at any other positions with one or more groups consisting of $C_1$-$C_{15}$ branched or straight chain alkyl, $C_1$-$C_{15}$ branched or straight chain alkoxy and halogen; T is selected from the group consisting of hydrogen and

wherein $R_1$ is selected from the group consisting of hydrogen, $C_1$-$C_4$ branched or straight chain alkyl, $C_1$-$C_4$ branched or straight chain alkoxy and $C_1$-$C_4$ branched or straight chain alkylamino; Y is selected from the group of bivalent radicals consisting of —$(CH_2)_p$— and —$(CHR)_p$—, wherein p is an integer from 2 to 10 and the moiety —$(CHR)_p$— represents an alkylene chain substituted with one or more $C_1$-$C_8$ alkyl groups or phenyl groups; Z is selected from the group consisting of

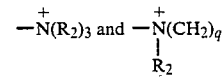

wherein q is an integer from 4-7 and $R_2$ may be the same or different and is selected from the group consisting of hydrogen and $C_1$-$C_4$ branched or straight chain alkyl.

The compounds of this invention can be prepared as racemic mixtures or as the individual R and S enantiomers. Such compounds have antihypertensive activity.

DETAILED DESCRIPTION OF THE INVENTION

In order to prepare the products of this invention, represented by the above formula 1, certain intermediate phenol and naphthalenol derivatives must be prepared as described hereinbelow in Flowsheet A, wherein the formula HO—X'—OH represents a dihydroxy benzene or naphthalene optionally substituted at any positions with one or more groups consisting of $C_1$-$C_{15}$ branched or straight chain alkyl, $C_1$-$C_{15}$ branched or straight chain alkoxy and halogen and wherein $R_3$ is a $C_1$-$C_{20}$ branched or straight chain alkyl group or benzyl group and J is a halogen atom (I, Br or Cl). According to Flowsheet A a dihydroxy compound 2 is alkylated with one equivalent of an alkyl halide 3 using sodium hydride in an inert solvent such as dimethylformamide to give the desired monoalkylated compound 4 and the dialkylated compound 5. In those cases where 2 is a symmetrical compound the resulting reaction mixture is composed of unreacted 2, monoalkylated compound 4 and dialkylated compound 5. The desired monoalkylated compound 4 can be separated from the mixture by a combination of short path distillation and recrystallization and, if necessary, chromatography. In those cases where compound 2 is not symmetrical, two monoalkylated regio isomers are obtained in addition to the dialkylated compounds. The monoalkylated compounds can be isolated by a combination of short path distillation and recrystallization. The resulting regio isomers can then be separated by various chromatographic techniques well known in the art.

FLOWSHEET A

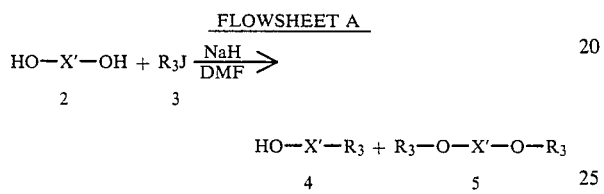

The compounds of this invention represented by structure 20 are prepared as outlined hereinbelow in Flowsheet B, wherein X', T, Y, Z, R$_3$, R$_1$, p, q, and R$_2$ are as defined above. The reaction of solketal 6 with mesyl chloride using an amine base such as triethylamine in an inert solvent such as methylene chloride or diethyl ether gives the mesylate 7. Treatment of the phenol or naphthalenol 4 with sodium hydride in an inert solvent such as dimethylformamide forms the sodium salt which reacts with mesylate 7 (if necessary sodium iodide is added to accelerate the reaction) to give the compound 8. The diol protecting of 8 can be removed using p-toluenesulfonic acid or an acidic ion exchange resin in methanol to give the diol 9. The diol 9 is reacted with a reagent which only functionalizes the primary hydroxyl group; one such reagent is p-anisylchlorodiphenylmethane 10 in pyridine or mixed solvent containing pyridine; this provides the monoprotected compound 11. This is converted to the compound 12 by alkylation with benzyl bromide using sodium hydride in an inert solvent. Treatment of 12 with methanol and an acidic catalyst such as p-toluenesulfonic acid or an acidic ion exchange resin gives the alcohol 13. The reaction of 13 with the phosphorous reagents 14a or 14b in an inert solvent such as carbon tetrachloride with a base such as triethylamine gives, after hydrolysis in a buffer such as aqueous sodium acetate, the phosphate compound 15. The reaction of 15 with amines 16a or 16b in a refluxing inert solvent or in a bomb at elevated temperatures affords compound 17. The benzyl protecting group of 17 is removed by hydrogenolysis to give the alcohol 18. Representative alkyl amines capable of being used in the present process are shown in Table III following Example 54 herein.

The compounds represented by the formula 18 can be converted to compounds 20 of this invention wherein R$_1$ is an alkyl group by the reaction of 18 with an anhydride 19a in the presence of a base catalyst such as triethylamine in an inert solvent such as chloroform.

The compounds represented by the formula 18 can be converted to compounds 20 of this invention wherein R$_1$ is a C$_1$-C$_4$ alkoxy group by the reaction of 18 with a pyrocarbonate 19c in the absence of solvent at elevated temperature (about 50°–150° C.).

The compounds represented by the formula 18 can be converted to compounds 20 of this invention wherein R$_1$ is hydrogen by the reaction of 18 with about 97% formic acid at room terperature for about 3 to 7 days.

The compounds represented by the formula 18 can be converted to compounds 20 of this invention wherein R$_1$ is a C$_1$-C$_4$ alkylamino group by treatment of 18 with an isocyanate 19b in an inert solvent such as toluene at about 25°–100° C. for about 1–7 days.

Since compound 6 is available in either the optically active R or S forms, or in the optically inactive racemic form, the compounds of this invention represented by the formula 20 can be prepared in the corresponding optically active R and S configurations or in the optically inactive racemic form by choosing the proper starting material [E. Baer, BIOCHEMICAL PREP., 2: 31 (1952); M. E. Jung and T. J. Shaw, J. AMER. CHEM. SOC., 102: 6304 (1980)].

FLOWSHEET B

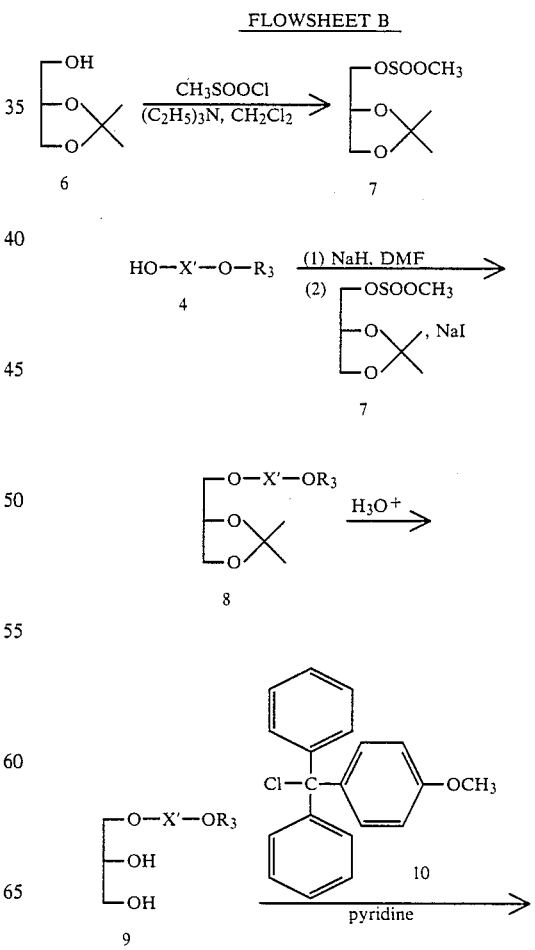

-continued
FLOWSHEET B

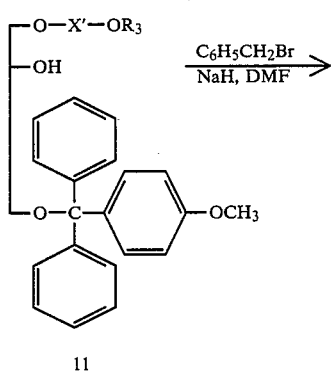

11

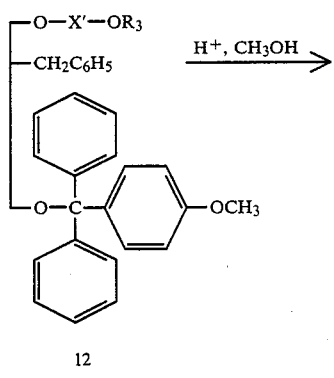

12

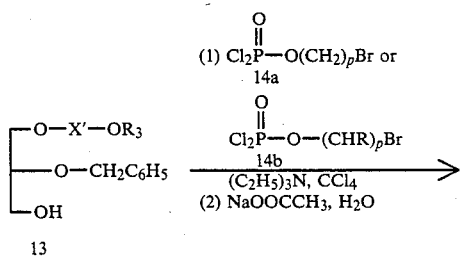

13

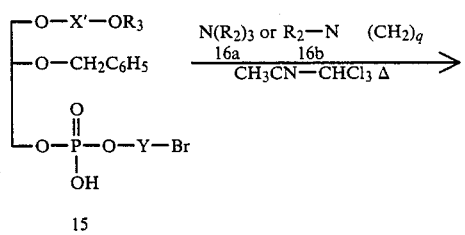

15

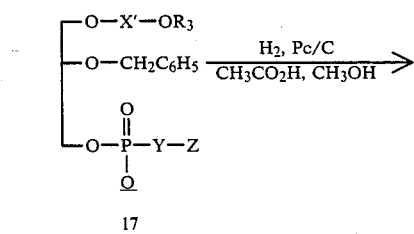

17

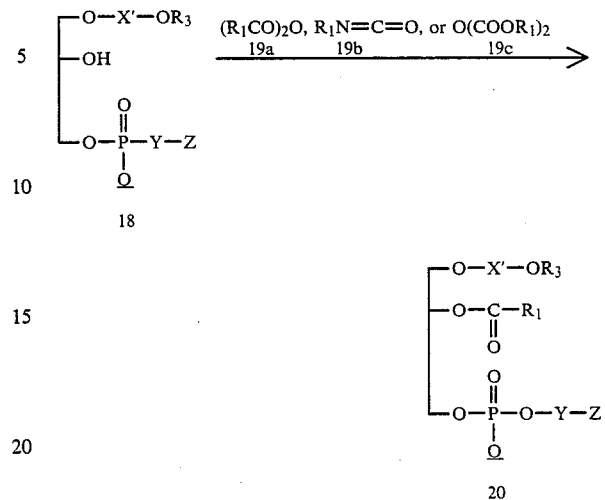

18

20

In those cases where $R_3$ is a benzyl group, a modified method is used to prepare the compounds of this invention as shown below in Flowsheet C. The reaction of 11 with an anhydride 19a using an amine base such as triethylamine in an inert solvent gives the compound 21. Removal of the p-methoxytrityl group of 21 without migration of the acyl moiety is accomplished by the boric acid-silic acid chromatographic technique of D. Buchnea, LIPIDS, 9, 55 (1974). The phosphate group is then introduced as described above. Finally, reaction with amines 16a and 16b gives the compounds of this invention represented by formula 24.

FLOWSHEET C

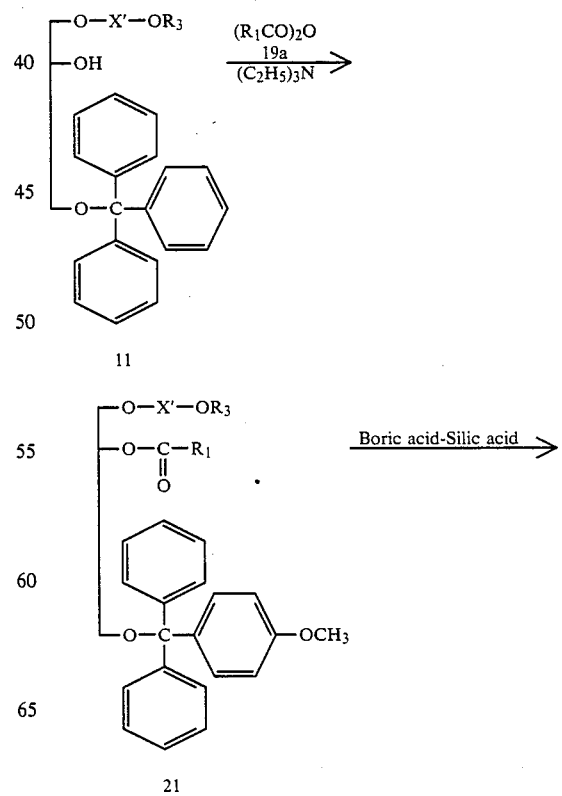

21

-continued
FLOWSHEET C

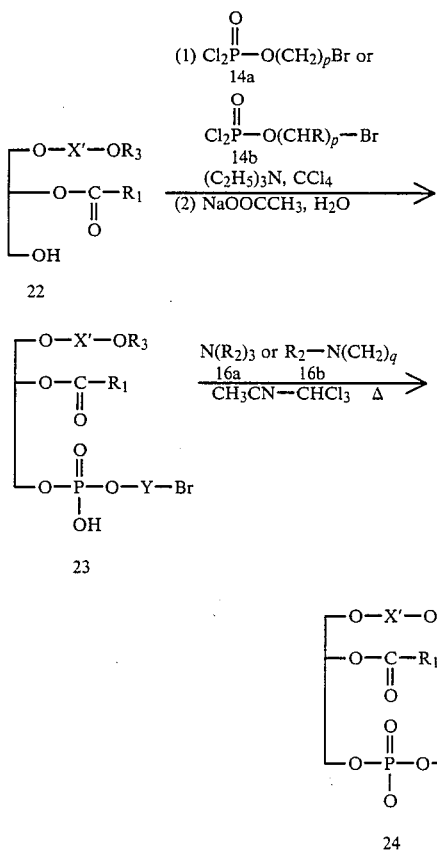

The methods for the preparation of the phosphorous reagents 14a and 14b used to prepare the compounds of this invention are described in detail in a copending application for U.S. Pat. Ser. No. 457,097, filed Jan. 10, 1983, which issued as U.S. Pat. No. 4,640,913 on Feb. 3, 1987, which is incorporated herein by reference, and in the following references: E. Baer and N. Z. Stanacey, J. BIOL. CHEM., 240, 3754 (1965); A. Eberhard and F. H. Westheimer, J. AMER. CHEM. SOC., 37, 253 (1965). By using such procedures the bromo alcohols of Table I are converted to the indicated phosphorodichlorodates.

TABLE I

| Bromo Alcohol | Phosphorodichlorodate |
|---|---|
| 2-bromoethanol | 2-bromoethyl phosphorodichlorodate |
| 3-bromopropanol | 3-bromopropyl phosphorodichlorodate |
| 2-bromopropanol | 2-bromopropyl phosphorodichlorodate |
| 2-bromo-1-methylethanol | 2-bromo-1-methylethyl phosphorodichlorodate |
| 4-bromobutanol | 4-bromobutyl phosphorodichlorodate |
| 5-bromopentanol | 5-bromopentylphosphorodichlorodate |
| 3-bromo-3-methylpropanol | 3-bromo-3-methylpropyl phosphorodichlorodate |
| 3-bromo-2-methylpropanol | 3-bromo-2-methylpropyl phosphorodichlorodate |
| 3-bromo-1-methylpropanol | 3-bromo-1-methylpropyl phosphorodichlorodate |
| 2-bromo-2-phenylethanol | 2-bromo-2-phenylethyl phosphorodichlorodate |
| 3-bromo-2-phenylpropanol | 3-bromo-2-phenylpropyl phos- |

TABLE I-continued

| Bromo Alcohol | Phosphorodichlorodate |
|---|---|
| | phorodichlorodate |

The compounds of the present invention are active as hypotensive agents as evidenced by their activity in the following test, the results of which are shown in Table II.

Under ether anesthesia, Weeks type cannulas (Peterson Technics) were surgically implanted in the abdominal aorta and vena cava of spontaneously hypertensive rats (Taconic Farms, Germantown, NY) and passed subcutaneously to the back of the neck where they were exteriorized. The cannulas were filled with saline, plugged and the rats returned to single cages where they were allowed food and water ad libitum.

At least three days following implantation of the cannulas, the rats were weighed and placed in Broome style restraining cages. The plug was removed from the aortic catheter which was connected to an arterial pressure transducer (Statham P23ID) using PE 100 polyethylene tubing and a stepdown connector fabricated from stainless steel hypodermic tubing. Mean arterial blood pressure was obtained by electrical damping of the pulse pressure channel. Heart rate was obtained from a tachograph triggered by the pulse pressure channel. All parameters were monitored on a Grass physiological recorder (Model 7).

The plug was removed from the vena cava catheter and a PE 20 polyethylene tubing extension was added using a piece of stainless steel hypodermic tubing. The other end was terminated with a 27G needle and one ml syringe.

All drugs were dissolved in saline or a mixture of ethanol and saline (25:75 V:V) such that the volume injected intravenously was about 0.1 ml/100 g body weight. All drugs were flushed in with about 0.2 ml saline. Blood pressure was continually monitored both before and after introduction of the test compound.

TABLE II

| Compound | Dose (μg/kg) | No. of Rats | Peak Δ Mean Arterial Blood Pressure (mmHg) |
|---|---|---|---|
| 7-[[[5-(dodecyloxy)-1-naphthalenyl]oxy]methyl]-4-hydroxy-N,N,N—trimethyl-9-oxo-3,5,8-trioxa-4-phosphadecan-1-aminium, 4-oxide, hydroxide, inner salt | 10 | 4 | −19.6 |
| | 30 | 4 | −45.9 |
| | 100 | 4 | −79.8 |
| | 300 | 4 | −95.9 |
| 7-[[[7-(dodecyloxy)-2-naphthalenyl]oxy]methyl]-4-hydroxy-N,N,N—trimethyl-9-oxo-3,5,8-trioxa-4-phosphadecan-1-aminium, 4-oxide, hydroxide, inner salt | 1 | 3 | −11.0 |
| | 3 | 3 | −44.3 |
| | 10 | 3 | −74.3 |
| 7-[[[4-(dodecyloxy)-1-naphthalenyl]oxy]methyl]-4-hydroxy-N,N,N—trimethyl-9-oxo-3,5,8-trioxa-4-phosphadecan-1-aminium, 4-oxide, hydroxide, inner salt | 10 | 4 | −6.8 |
| | 30 | 4 | −16.1 |
| | 100 | 4 | −30.5 |
| | 300 | 4 | −46.0 |
| 7-[[[6-(dodecyloxy)-2-naphthalenyl]oxy]methyl]-4-hydroxy-N,N,N—trimethyl-9-oxo-3,5,8-trioxa-4-phosphadecan-1-aminium, 4-oxide, hydroxide, inner | 10 | 5 | −13.9 |
| | 30 | 5 | −26.7 |
| | 300 | 5 | −61.4 |
| | 1000 | 5 | −89.3 |

TABLE II-continued

| Compound | Dose (μg/kg) | No. of Rats | Peak Δ Mean Arterial Blood Pressure (mmHg) |
|---|---|---|---|
| salt | | | |
| 7-[[3-(dodecyloxy)-2-meth- | 0.1 | 4 | −8.1 |
| ylphenoxy]methyl]-4- | 0.3 | 4 | −47.7 |
| hydroxy-N,N,N—triethyl-9- | 1.0 | 4 | −79.9 |
| oxo-3,5,8-trioxa-4-phos- | 3.0 | 4 | −110.4 |
| phadecan-1-aminium, | | | |
| 4-oxide, hydroxide, inner | | | |
| salt | | | |
| 7-[[4-(phenylmethoxy)phen- | 10 | 4 | −12.9 |
| oxy]methyl]-4-hydroxy- | 30 | 4 | −23.6 |
| N,N,N—trimethyl-9-oxo- | 100 | 4 | −37.8 |
| 3,5,8-trioxa-4-phosphadec- | 300 | 4 | −70.4 |
| an-1-aminium, 4-oxide, | 1000 | 4 | −89.7 |
| hydroxide, inner salt | | | |

When the compounds are employed for the above utility, they may be combined with one or more pharmaceutically acceptable carriers, e.g., solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 0.05% up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.005 mg to about 100 mg/kg of animal body weight, preferably given in divided doses two to four times a day, or in sustained release form. For most large mammals the total daily dosage is from about 500 μg to about 5,000 mg preferably from about 350 μg to 3,500 mg. Dosage forms suitable for internal use comprise from about 25 μg to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation. A decided practical advantage is that these active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, e.g., vitamin E, ascorbic acid, BHT and BHA.

The preferred pharmaceutical compositions from the stand-point of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations should contain a preservative to prevent the growth of microorganisms.

The pharmaceutical forms suitable for injection use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

In addition to the above utilities, some of the compounds of this invention (such as 15 of flowsheet A and 32 of flowsheet B) are useful for the preparation of other compounds of this invention.

In particular, it has been found that 7-[[3-(dodecyloxy)-4,6-(di-t-butyl)phenoxy]methyl]-4-hydroxy-N,N,N-trimethyl-9-oxo-3,5,8-trioxa-4-phosphadecan-1-aminium, 4-oxide, hydroxide, inner salt can decrease mean arterial blood pressure 50 mm Hg in spontaneously hypertensive rats at a dose of about 13.0 μg/Kg, but without platelet aggregation at such dose.

The invention will be more fully described in conjunction with the following specific examples which are not to be construed as limiting the scope of the invention. In addition, other applicable procedures are described in the aforementioned copending application, Ser. No. 457,097, filed Jan. 10, 1983, which issued as U.S. Pat. No. 4,640,913 on Feb. 3, 1987.

EXAMPLE 1

5-(Dodecyloxy)-1-naphthalenol

To a suspension of 9.14 g of washed (hexane) 50% sodium hydride in 100 ml of dimethylformamide containing 2.28 g of sodium iodide, under argon, was added with stirring a solution of 24.4 g of 1,5-dihydroxynaphthalene in a mixture of 200 ml of dimethylformamide and 100 ml of tetrahydrofuran over 30 minutes. After stirring for an additional 30 minutes, 37.97 g of n-dodecyl bromide was added. This mixture was stirred 2 hours, then poured into water and extracted with ether. The ether layer was separated, dried over magnesium sulfate and activated charcoal and filtered through silica gel. The solvent was removed and the residue extracted four times with 800 ml of boiling hexane. The hexane solutions were filtered while hot, the solvent removed and the residue recrystallized from hexane, giving 13 g of the desired compound as a grey powder, mp 79°–83° C.

EXAMPLE 2

3-(Dodecyloxy)-2-methylphenol

To a stirred suspension of 36.23 g of washed (hexane) 50% sodium hydride in 300 ml of dimethylformamide, under argon, was added over 1.5 hours a solution of 75 g of 2-methylresorcinol in a mixture of 200 ml of dimethylformamide and 100 ml of tetrahydrofuran. This solution was cooled in an ice bath and 9.06 g of sodium iodide was added followed by the addition of 150.58 g of n-dodecyl bromide over one hour. This mixture was stirred at room temperature for 2.5 hours, then quenched with dilute hydrochloric acid and extracted with ether. The ether extract was dried, filtered through silica gel and the solvent removed. The residue was distilled via a Kugelrohr at 0.1 mm. The fraction distilled at 170°–200° C. was redistilled at 170° C., 0.1 mm. The distillate was passed through a column of silica gel, eluting with ether:hexane (1:1). The solvent was removed and the residue redistilled at 170° C., 0.1 mm giving 53.5 g. of the desired compound as an oil which crystallized, mp 38°–39° C.

EXAMPLE 3

7-(Dodecyloxy)-2-naphthalenol

To a suspension of 19.47 g of washed (hexane) 50% sodium hydride in 200 ml of dimethylformamide, under argon, was added with stirring a solution of 50 g of 2,7-dihydroxynaphthalene in a mixture of 100 ml of dimethylformamide and 200 ml of tetrahydrofuran over one hour. The mixture was cooled to 0° C. and 92.47 g of n-dodecyl iodide was added. The mixture was heated to 60° C. and then stirred at room temperature overnight; diluted with hydrochloric acid and extracted with ether. The ether extract was dried over magnesium sulfate and activated charcoal and the solvent removed. The residue was fractionated on a Kugelrohr. The fraction at 170°–250° C. was collected as a solid and recrystallized from hexane, giving 10.4 g of the desired compound as a white solid, mp 97°–98° C.

EXAMPLE 4

4-(Dodecyloxy)-1-naphthalenol

To a stirred suspension of 17.25 g of washed (hexane) 50% sodium hydride in 200 ml of dimethylformamide, under argon, was added a solution of 44.3 g of 1,4-dihydroxynaphthalene in a mixture of 200 ml of dimethylformamide and 100 ml of tetrahydrofuran over one hour. The mixture was cooled to 0° C. and then 4.15 g of sodium iodide and 68.93 g of n-dodecyl bromide were added. This mixture was stirred at room temperature for 2 hours, water was added, the mixture was acidified with sulfuric acid and then extracted with ether. The ether extract was dried, the solvent removed and the residue distilled on a Kugelrohr. The fraction distilling at 160°–230° C. (0.1 mm) was collected and redistilled. The fraction distilling at 200°–210° C. (0.1 mm) was collected and recrystallized from hexanes, giving 27 g of the desired compound, mp 86°–88° C.

EXAMPLE 5

6-(Dodecyloxy)-2-naphthalenol

To a suspension of 14.98 g of washed (hexane) 50% sodium hydride in 160 ml of dimethylformamide, under argon, was added with stirring over one hour, a solution of 40 g of 2,6-dihydroxynaphthalene in 150 ml of tetrahydrofuran and 80 ml of dimethylformamide. To this solution was added 3.74 g of sodium iodide and 62.24 g of n-dodecyl bromide. The mixture was heated to 50° C., then stirred at room temperature for 4 hours, water was added and the mixture extracted with ether and ethyl acetate. The organic extract was dried, the solvent removed and the residue mixed with hot carbon tetrachloride and filtered. The solvent was removed from the filtrate and the residue was purified by HPLC, eluting with chloroform:hexane (2:3). The solid was recrystallized from hexane, giving 3.5 g of the desired compound, mp 85°–87° C.

EXAMPLE 6

2,4-Bis(1,1-dimethylethyl)-5-(dodecyloxy)phenol

To a suspension of 21.04 g of washed (hexane) 50% sodium hydride in 200 ml of dimethylformamide, under argon, was added with stirring 5.06 g of sodium iodide followed by the dropwise addition of a solution of 4,6-di-tertiary-butylresorcinol in 200 ml of dimethylformamide and 150 ml of tetrahydrofuran over one hour. Then, 84.08 g of n-dodecyl bromide was added dropwise over ½ hour and this mixture was stirred overnight. The mixture was poured into water and extracted with ether. The ether extract was washed with water, dried and the solvent removed. The residue was distilled on a Kugelrohr collecting the distillate from 180°–210° C. (0.5 mm). This was redistilled, collecting the fraction 180°–205° C. (0.5 mm), which gave 38 g of the desired product as an orange oil.

EXAMPLE 7

3-[[5-(Dodecyloxy)-1-naphthalenyl]oxy]-1,2-propanediol

To a suspension of 2.19 g of 50% sodium hydride in 80 ml of dimethylformamide, under argon, was added with stirring a solution of 12 g of 5-(dodecyloxy)-1-naphthalenol in 60 ml of tetrahydrofuran over ½ hour. A 2 g portion of sodium iodide and 9.77 g of solketal mesylate were added and the mixture was stirred overnight. The mixture was diluted with water and extracted with ether. The ether extract was washed with dilute sodium hydroxide, then brine, dried, filtered through silica gel and the solvent removed. The residue was refluxed in a mixture of 100 ml of methanol, 16 ml of water and 1 ml of concentrated sulfuric acid for one hour, then cooled and the solid collected. This solid was dissolved in boiling chloroform containing magnesium sulfate and activated carbon and filtered through diatomaceous earth. The filtrate was evaporated and the residue recyrstallized from carbon tetrachloride, giving 8 g of the desired compound as an off-white solid, mp 143°–144° C.

EXAMPLE 8

3-[3-(Dodecyloxy)-2-methylphenoxy]-1,2-propanediol

To a stirred suspension of 5.74 g of washed (hexane) 50% sodium hydride in 175 ml of dimethylformamide, under argon, was added 28 g of 3-(dodecyloxy)-2-methyl-phenol in 120 ml of tetrahydrofuran over one hour. A 4 g portion of sodium iodide and 23.29 g of solketal mesylate were added, the mixture was stirred at 80° C. overnight, then cooled and water was added. This mixture was extracted with ether. The ether extract was washed with dilute sodium hydroxide, then brine, dried, filtered through silica gel and the solvent removed. The residue was refluxed in a mixture of 200 ml of methanol, 32 ml of water and 2 ml of concentrated sulfuric acid for one hour, then cooled and the solid collected and recrystallized from methanol, giving 24.4 g of the desired compound, mp 76°–78° C.

EXAMPLE 9

3-[[7-(Dodecyloxy)-2-naphthalenyl]oxy]-1,2-propanediol

To a stirred suspension of 1.83 g of washed (hexane) 50% sodium hydride in 80 ml of dimethyformamide, under argon, was added 10 g of 7-(dodecyloxy)-2-naphthalenol, 0.46 g of sodium iodide and 40 ml of tetrahydrofuran. After 15 minutes 7.14 g of solketal mesylate was added. This mixture was stirred at 90° C. overnight, then diluted with water and extracted with ether. The ether extract was dried and evaporated. The residue was refluxed for one hour in a mixture of 100 ml of methanol, 16 ml of water and 1 ml of concentrated sulfuric acid, then evaporated. The residue was dissolved in chloroform, washed with water, dried and the solvent removed. The residue was recrystallized from methanol giving the desired compound as an off-white solid, mp 92°–94° C.

EXAMPLE 10

3-[[4-(Dodecyloxy)-1-naphthalenyl]oxy]-1,2-propanediol

To a stirred suspension of 3.65 g of washed (hexane) 50% sodium hydride in 60 ml of dimethylformamide, under argon, was added a solution of 20 g of 4-(dodecyloxy)-1-naphthalenol in 80 ml of tetrahydrofuran over ½ hour followed by 0.91 g of sodium iodide and 14.81 g of solketal mesylate. The mixture was heated at 80° C. for 8 hours, then stirred at room temperature overnight, water was added and the mixture extracted with ether. The ether extract was dried, evaporated and the residue refluxed for one hour in a mixture of 200 ml of methanol, 32 ml of water and 2 ml of concentrated sulfuric acid. The solvent was removed, the residue dissolved in chloroform, washed with water, dried and filtered through silica gel. The solvent was removed and the residue recrystallized from methanol, giving 21 g of the desired compound as a white solid, mp 102°–104° C.

EXAMPLE 11

3-[[6-(Dodecyloxy)-2-naphthalenyl]oxy]-1,2-propanediol

To a stirred suspension of 2.1 g of washed (hexane) 50% sodium hydride in 100 ml of dimethylformamide and 50 ml of tetrahydrofuran, under argon, was added 11.5 g of 6-(dodecyloxy)-2-naphthalenol, 0.52 g of sodium iodide and 8.52 g of solketal mesylate. After stirring one hour the mixture was heated at 85° C. overnight, then water was added and the mixture was extracted with ether. The ether extract was dried, evaporated and the residue refluxed for one hour in a mixture of 100 ml of methanol, 16 ml of water and 1 ml of concentrated sulfuric acid. The solvent was removed, the residue dissolved in chloroform, washed with water, dried and evaporated. This residue was recrystallized from methanol, giving 12.0 g of the desired compound as a white solid, mp 133°–134° C.

EXAMPLE 12

3-[2,4-Bis(1,1-dimethylethyl)-5(dodecyloxy)phenoxy]-1,2-propanediol

To a suspension of 3.22 g of washed (hexane) 50% sodium hydride and 0.81 g of sodium iodide in 200 ml of dimethylformamide, under argon, was added with stirring over one hour a solution of 21 g of 2,4-bis(1,1-dimethylethyl)-5-(dodecyloxy)phenol in 100 ml of tetrahydrofuran followed by 13.08 g of solketal mesylate. The mixture was heated at 85° C. overnight, then water was added and the mixture was extracted with ether. The ether extract was washed with water, dried and the solvent removed. The residue was refluxed for one hour in a mixture of 200 ml of methanol, 32 ml of water and 2 ml of concentrated sulfuric acid. The methanol was removed, the residue extracted with ether, the extract dried and then evaporated. The residue was recrystallized twice from methanol-water, giving 20 g of the desired compound as an off-white solid, mp 35°–37° C.

EXAMPLE 13

1-[[5-(Dodecyloxy)-1-naphthalenyl]oxy]-3-[(4-methoxyphenyl)diphenylmethoxy]-2-propanol A solution of 7.5 g of 3-[[5-dodecyloxy)-1-naphthalenyl]oxy]-1,2-propanediol in 10 ml of pyridine and 30 ml of tetrahydrofuran was warmed on a steam bath until the solid dissolved. A 6.04 g portion of p-methoxytrityl chloride was added, the mixture was allowed to stand overnight and then the solvent was removed. The residue was mixed with ethyl acetate and water. The organic layer was separated, washed with brine, dried and the solvent removed. The residue was used in Example 19 without further purification.

EXAMPLE 14

1-[3-(Dodecyloxy)-2-methylphenoxy]-3-[(4-methoxyphenyl)-diphenylmethoxy]-2-propanol A mixture of 20 g of 3-[3-(dodecyloxy)-2-methylphenoxy]-1,2-propanediol, 20.22 g of p-methoxytrityl chloride, 30 ml of pyridine and 90 ml of tetrahydrofuran was allowed to stand for 72 hours, then the solvent was removed. The residue was mixed with water and extracted with ether. The ether extract was washed with water, then brine, dried and the solvent removed. The residue was used without further purification in Example 20.

EXAMPLE 15

1-[[7-(Dodecyloxy)-2-naphthalenyl]oxy]-3-[(4-methoxyphenyl)diphenylmethoxy]-2-propanol A mixture of 9 g of 3-[[7-(dodecyloxy)-2-naphthalenyl]oxy]-1,2-propanediol, 8.63 g of p-methoxytrityl chloride, 15 ml of pyridine and 40 ml of tetrahydrofuran was allowed to stand overnight. The tetrahydrofuran was removed, the remainder poured into water and extracted with ether. The ether extract was dried, evaporated and the residue dried in vacuo and used without further purification in Example 21.

EXAMPLE 16

1-[[4-(Dodecyloxy)-1-naphthalenyl]oxy]-3-[(4-methoxyphenyl)diphenylmethoxy]-2-propanol A mixture of 15 g of 3-[[4-(dodecyloxy)-1-naphthalenyl]oxy]-1,2-propanediol, 14.38 g of p-methoxytrityl chloride, 40 ml of pyridine and 100 ml of tetrahydrofuran was allowed to stand overnight. The tetrahydrofuran was removed, the remainder poured into water and extracted with ether. The ether extracted was dried and evaporated giving a green oil which was used without further purification in Example 22.

EXAMPLE 17

1-[[6-(Dodecyloxy)-2-naphthalenyl]oxy]-3-[(4-methoxyphenyl)diphenylmethoxy]-2-propanol A mixture of 10 g of 3-[[6-(dodecyloxy)-2-naphthalenyl]oxy]-1,2-propanediol, 9.59 g of p-methoxytrityl chloride, 30 ml of pyridine and 75 ml of tetrahydrofuran was allowed to stand overnight, then the solvent was removed. The residue was dissolved in ether, washed with water, then brine, dried and the solvent removed. The residue was used without further purification in Example 23.

EXAMPLE 18

1-[2,4-Bis(1,1-dimethylethyl)-5-(dodecyloxy)phenoxy]-3-[(4-methoxyphenyl)diphenylmethoxy]-2-propanol A mixture of 15 g of 3-[2,4-bis(1,1-dimethylethyl)-5-(dodecyloxy)phenoxy]-1,2-propanediol, 12.46 g of p-methoxytrityl chloride, 40 ml of pyridine and 100 ml of tetrahydrofuran was allowed to stand overnight, then the solvent was removed. Water was added and the mixture extracted with ether. The ether extract was dried, evaporated and the residue dried in vacuo, giving an oil which was used without further purification in Example 24.

EXAMPLE 19

3-[[5-(Dodecyloxy)-1-naphthalenyl]oxy]-2-(phenylmethoxy)-1-propanol

To a suspension of 1.34 g of washed (hexane) 50% sodium hydride in 60 ml of dimethylformamide containing 4.78 g of benzyl bromide, under argon, was added with stirring a solution of 9.96 g of 1-[[5-(dodecyloxy)-1-naphthalenyl]oxy]-3-[(4-methoxyphenyl)diphenylmethoxy]-2-propanol in 30 ml of tetrahydrofuran. After stirring 2 hours, water was added and the mixture was extracted with ethyl acetate. The organic extract was dried and the solvent removed. The residue was dissolved in a mixture of 120 ml of methanol and 60 ml of chloroform, heated to boiling and 4 g of strongly acidic ion exchange resin was added. This mixture was stirred for one hour, then filtered and the solvent removed. The residue was purified by HPLC using hexane:ethyl acetate (4:1) giving 7.5 g of the desired compound as a white solid, mp 60°–62° C.

EXAMPLE 20

3-[3-(Dodecyloxy)-2-methylphenoxy]-2-(phenylmethoxy)-1-propanol

To a stirred mixture of 3.93 g of washed (hexane) 50% sodium hydride and 14 g of benzyl bromide in 90 ml of dimethylformamide, under argon, was added 34.86 g of 1-[3-(dodecyloxy)-2-methylphenoxy]-3-[(4-methoxyphenyl)diphenylmethoxy]-2-propanol over 45 minutes. After stirring for 2 hours, water was added and the mixture was extracted with ether. The ether extract was washed with water, dried and the solvent removed. The residue was heated to boiling in a mixture of 200 ml of methanol, 50 ml of chloroform and 20 g of a strongly acidic ion exchange resin was added. This mixture was stirred for two hours, filtered and the solvent removed. The residue was purified by HPLC, eluting with hexane:ethyl acetate (4:1), giving 18.47 g of the desired compound as a white solid, mp 50°–51° C.

EXAMPLE 21

3-[[7-(Dodecyloxy)-2-naphthalenyl]oxy]-2-(phenylmethoxy)-1-propanol

To a stirred suspension of 1.6 g of washed (hexane) 50% sodium hydride in 45 ml of dimethylformamide, under argon, was added a mixture of 5.7 g of benzyl bromide and 1-[[7-(dodecyloxy)-2-naphthalenyl]oxy]-3-[(4-methoxyphenyl)diphenylmethoxy]-2-propanol in 30 ml of tetrahydrofuran. The mixture was stirred for 2 hours, then water was added and the mixture was extracted with ether. The ether extract was dried, the solvent removed and the residual oil dissolved with heat in a mixture of 100 ml of methanol and 50 ml of chloroform. A 10 g portion of a strongly acidic ion exchange resin was added to the hot solution which was then stirred for one hour, filtered and the solvent removed. The residue was purified by HPLC eluting with ethyl acetate:hexane (1:4) giving 7.25 g of the desired compound as an oil which crystallized on standing, mp 54°–56° C.

EXAMPLE 22

3-[[4-(Dodecyloxy)-1-naphthalenyl]oxy]-2-(phenylmethoxy)-1-propanol

To a stirred suspension of 2.68 g of washed (hexane) 50% sodium hydride and 9.54 g of benzyl bromide in 80 ml of dimethylformamide, under argon, was added a solution of 25.1 g of 1-[[4-(dodecyloxy)-1-naphthalenyl]-oxy]-3-[(4-methoxyphenyl)diphenylmethoxy]-2-propanol in 60 ml of tetrahydrofuran over 15 minutes. The mixture was stirred one hour, water was added and this mixture was extracted with ether. The ether extract was dried, evaporated and the residue heated to reflux in a mixture of 170 ml of methanol and 80 ml of chloroform. A 15 g portion of a strongly acidic ion exchange resin was added, this mixture was stirred one hour, then filtered and the solvent removed. The residue was purified by HPLC eluting with ethyl acetate:hexane (1:4) giving 14.33 g of the desired compound as an oil which crystallized on standing, mp 42°–43° C.

EXAMPLE 23

3-[[6-(Dodecyloxy)-2-naphthalenyl]oxy]-2-(phenylmethoxy)-1-propanol

To a stirred suspension of 1.79 g of washed (hexane) 50% sodium hydride in 55 ml of dimethylformamide, under argon, was added 6.37 g of benzyl bromide and a solution of 16.77 g of 1-[[6-(dodecyloxy)-2-naphthalenyl]-oxy]-3-[(4-methoxyphenyl)diphenylmethoxy]-2-propanol in 40 ml of tetrahydrofuran. The mixture was heated to 55° C., then stirred at room temperature for 3 hours, water was added and the mixture was extracted with ether. The ether extract was evaporated and the residue heated to reflux in a mixture of 150 ml of methanol and 60 ml of chloroform. A 13 g portion of a strongly acidic ion exchange resin was added and after stirring for one hour the solvent was removed. The residue was purified by HPLC eluting with ethyl acetate:hexane (1:4) giving 10.64 g of the desired compound as an off-white solid, mp 74°–76° C.

EXAMPLE 24

3-[2,4-Bis(1,1-dimethylethyl)-5-(dodecyloxy)phenoxy]-2-(phenylmethoxy)-1-propanol To a stirred suspension of 2.44 g of washed (hexane) 50% sodium hydride in 40 ml of dimethylformamide containing 8.7 g of benzyl bromide, under argon, was added over 15 minutes a solution of 24.98 g of 1-[2,4-bis(1,1-dimethylethyl)-5-(dodecyloxy)phenoxy]-3-[(4-methoxyphenyl)-diphenylmethoxy]-2-propanol in 40 ml of dimethylformamide and 60 ml of tetrahydrofuran. The mixture was stirred 3 hours, water was added, the mixture was extracted with ether and the ether extract evaporated. The residue was heated to boiling in 170 ml of methanol and 80 ml of chloroform, 15 g of a strongly acidic ion exchange resin was added and the mixture stirred for one hour. The solvent was removed and the residue was purified by HPLC eluting with hexane:ether (7:1) giving the desired compound as an oil.

EXAMPLE 25

7-[[[5-(Dodecyloxy)-1-naphthalenyl]oxy]methyl]-4-hydroxy-N,N,N-trimethyl-9-phenyl-3,5,8-trioxa-4-phosphanonan-1-aminium, 4-oxide, hydroxide, inner salt A 3.5 g portion of 3-[[5-(dodecyloxy)-1-naphthalenyl]oxy]-2-(phenylmethoxy)-1-propanol, 2.58 g of 2-bromoethyl phosphorodichlorodate and 1.08 g of triethylamine in 50 ml of carbon tetrachloride was stirred for 1.5 hours, then filtered and the solvent removed. The residue was stirred in a mixture of 100 ml of 0.5 M aqueous sodium acetate and 100 ml of tetrahydrofuran for 1.5 hours, then the tetrahydrofuran was removed. The residue was acidified with hydrochloric acid and extracted with ether. The ether extract was dried, the solvent removed and the residue refluxed in a mixture of 100 ml of acetonitrile, 90 ml of methylene chloride and 50 g of trimethylamine for 4 hours. The solvent was removed and the residue stirred for one hour in a mixture of 100 ml of methanol, 4 g of a weak basic ion exchange resin and 0.7 g of silver carbonate. This mixture was filtered, the solvent removed and the residue chromatographed on silica gel, eluting first with chloroform:methanol (7:3) to remove the higher Rf components and then with chloroform:methanol:water (70:-30:5) to elute the product. The solvent was removed, giving 3 g of the desired compound as a thick oil.

EXAMPLE 26

3-[[3-(Dodecyloxy)-2-methylphenoxy]methyl]-6-hydroxy-N,N,N-trimethyl-1-phenyl-2,5,7-trioxa-6-phosphanonan-9-aminium, 6-oxide, hydroxide, inner salt A mixture of 9.47 g of 3-[3-(dodecyloxy)-2-methylphenoxy]-2-(phenylmethoxy)-1-propanol, 7.52 g of 2-bromoethyl phosphorodichlorodate and 3.15 g of triethylamine in 50 ml of carbon tetrachloride was stirred for 2 hours, filtered and the solvent removed. The residue was stirred in a mixture of 270 ml of 0.5 M aqueous sodium acetate and 270 ml of tetrahydrofuran for 2 hours. The tetrahydrofuran was removed, the residue acidified with hydrochloric acid and extracted with ether. The ether extract was evaporated and the residue refluxed in a mixture of 250 ml of acetonitrile, 200 ml of chloroform and 100 g of trimethylamine for 3 hours, then allowed to stand at room temperature overnight. The solvent was removed and the residue stirred for 1.5 hours in 200 ml of methanol containing 8 g of a weak basic ion exchange resin and 2 g of silver carbonate. This mixture was filtered and the solvent removed. The residue was chromatographed on silica gel eluting first with chloroform:methanol (8:2) to remove the higher Rf components and then with chloroform:methanol:water (70:-30:5) giving 7.2 g of the desired compound as an oil.

EXAMPLE 27

3-[[[7-(Dodecyloxy)-2-naphthalenyl]oxy]methyl]-6-hydroxy-N,N,N-trimethyl-1-phenyl-2,5,7-trioxa-6-phosphanonan-9-aminium, 6-oxide, hydroxide, inner salt A mixture of 6.25 g of 3-[[7-(dodecyloxy)-2-naphthalenyl]oxy]-2-(phenylmethoxy)-1-propanol, 4.6 g of 2-bromoethyl phosphorodichlorodate and 1.93 g of triethylamine in 100 ml of carbon tetrachloride was stirred for 1.5 hours, filtered and the solvent removed. The residue was stirred in a mixture of 180 ml of 0.5 M aqueous sodium acetate and 180 ml of tetrahydrofuran. The tetrahydrofuran was removed, the remainder acidified with hydrochloric acid and ether extracted. The ether extract was dried, evaporated and the residue refluxed for 3 hours in a mixture of 150 ml of acetonitrile, 120 ml of chloroform and 50 g of trimethylamine. The solvent was removed and the residue stirred for one hour in 150 ml of methanol containing 1.5 g of silver carbonate and 6 g of a weak basic ion exchange resin. This mixture was filtered and the solvent removed. The residue was chromatographed on silica gel, eluting first with chloroform:methanol (7:3) to remove the higher Rf components and then with chloroform:methanol:water (70:30:5), giving 4.46 g of the desired compound as an oil.

EXAMPLE 28

3-[[[4-(Dodecyloxy)-1-naphthalenyl]oxy]methyl]-6-hydroxy-N,N,N-trimethyl-1-phenyl-2,5,7-trioxa-6-phosphanonan-9-aminium, 6-oxide, hydroxide, inner salt A mixture of 7.3 g of 3-[[4-(dodecyloxy)-1-naphthalenyl]oxy]-2-(phenylmethoxy)-1-propanol, 5.37 g of 2-bromoethyl phosphorodichlorodate and 2.25 g of triethylamine in 100 ml of carbon tetrachloride was stirred for 2 hours, filtered and the solvent removed. The residue was stirred for 1.5 hours in a mixture of 180 ml of 0.5 M aqueous sodium acetate and 180 ml of tetrahydrofuran. The tetrahydrofuran was removed, the remainder acidified with hydrochloric acid and extracted with ether. The ether extract was dried and evaporated, giving an oil which crystallized on standing. This solid was added to 150 ml of acetonitrile, 120 ml of chloroform and 100 g of trimethylamine, refluxed for 4 hours and the solvent removed. The residue was stirred in 200 ml of methanol containing 10 g of a weak basic ion exchange resin and 1 g of silver carbonate, then filtered and the solvent removed. The residue was chromatographed on 200 ml dry volume of silica gel, eluting first with chloroform:methanol (7:3) to remove higher Rf impurities and then with chloroform:methanol:water (70:30:5) to elute the product. The solvent was removed and ether was added, giving 6.5 g of the desired compound as a white solid.

EXAMPLE 29

3-[[[5-(Dodecyloxy)-1-naphthalenyl]oxy]methyl]-6-hydroxy-N,N,N-trimethyl-1-phenyl-2,5,7-trioxa-6-phosphanonan-9-aminium, 6-oxide, hydroxide, inner salt To 100 ml of carbon tetrachloride was added 6.6 g of 3-[[6-(dodecyloxy)-2-naphthalenyl]oxy]-2-(phenylmethoxy)-1-propanol, 4.86 g of 2-bromoethyl phosphorodichlorodate and 2.03 g of triethylamine. The mixture was stirred 3 hours, filtered and the solvent removed. The residue was stirred for one hour in a mixture of 180 ml of 0.5 M aqueous sodium acetate and 180 ml of tetrahydrofuran. The tetrahydrofuran was removed, the remainder acidified with hydrochloric acid and extracted with ether. The ether extract was dried, evaporated and the residue refluxed for 4 hours in a mixture of 150 ml of acetonitrile, 120 ml of chloroform and 50 g of trimethylamine. The solvent was removed and the residue stirred for 2 hours in 200 ml of methanol containing 1 g of silver carbonate and 8 g of a weak basic ion exchange resin. The mixture was filtered, the solvent removed and the residue chromatographed on silica gel, eluting first with chloroform:methanol (7:3) to remove the higher Rf components and then with chloroform:methanol:water (70:30:5), giving 5.42 g of the desired compound as a white foam.

EXAMPLE 30

3-[[2,4-Bis(1,1-dimethylethyl)-5-(dodecyloxy)phenoxy]-methyl]-6-hydroxy-N,N,N-trimethyl-1-phenyl-2,5,7-trioxa-6-phosphanonan-9-aminium, 6-oxide, hydroxide, inner salt A mixture of 4.5 g of 3-[2,4-bis(1,1-dimethylethyl)-5-(dodecyloxy)phenoxy]-2-(phenylmethoxy)-1-propanol, 2.94 g of 2-bromoethyl phosphorodichlorodate and 1.23 g of triethylamine in 100 ml of carbon tetrachloride was stirred for 2 hours, filtered and the solvent removed. The residue was stirred for 1.15 hours in a mixture of 170 ml of 0.5 M aqueous sodium acetate and 170 ml of tetrahydrofuran. The tetrahydrofuran was removed, the remainder acidified with hydrochloric acid and extracted with ether. The ether extract was washed with water, dried, evaporated and the residue refluxed for 4 hours in a mixture of 150 ml of acetonitrile, 120 ml of chloroform and 50 g of trimethylamine. The solvent was removed, the residue stirred in 150 ml of methanol containing 8 g of a weak basic ion exchange resin and 1 g of silver carbonate, filtered and the solvent removed. The residue was chromatographed on silica gel eluting first with chloroform:methanol (4:1) to remove the higher Rf components and then with chloroform:methanol:water (70:30:4), giving 4.61 g of the desired compound as an oil.

EXAMPLE 31

2-Bromopropyl-3-[[5-(dodecyloxy)-1-naphthalenyl]oxy]-2-(phenylmethoxy)propyl phosphoric acid ester To a solution of 2.47 g of 2-bromopropyl phosphorodichlorodate in 110 ml of carbon tetrachloride, cooled in an ice bath under argon, was added dropwise with stirring 5.5 ml of triethylamine. A solution of 3.4 g of 3-[[5-(dodecyloxy)-1-naphthalenyl]oxy]-2-(phenylmethoxy)-1-propanol in 15 ml of carbon tetrachloride was added dropwise. This mixture was stirred at 0° C. for 15 minutes, then at room temperature overnight, 110 ml of toluene was added and the mixture filtered through diatomaceous earth. The solvents were removed and the residual syrup dissolved in 110 ml of tetrahydrofuran and 110 ml of 0.5 M aqueous sodium acetate, stirred for 2 hours and the tetrahydrofuran removed in vacuo. The aqueous residue was acidified with hydrochloric acid and extracted twice with ether. The ether extracts were combined, washed with saturated aqueous sodium chloride, dried and evaporated. The resulting syrup was purified by chromatography on magnesium silicate, washing with chloroform to remove the mobiles and then eluting with 10% methanol in chloroform, giving 3.3 g of the desired compound as a syrup.

EXAMPLE 32

3-[[[5-(Dodecyloxy)-1-naphthalenyl]oxy]methyl]-6-hydroxy-N,N,N-trimethyl-1-phenyl-2,5,7-trioxa-6-phosphadecan-9-aminium, 6-oxide, hydroxide, inner salt A 3.2 g portion of 2-bromopropyl-3-[[5-(dodecyloxy)-1-naphthalenyl]oxy]-2-(phenylmethoxy)propyl phosphoric acid ester was dissolved in 25 ml of cold trimethylamine. A 15 ml portion of dimethylformamide was added, then 25 ml of trimethylamine. This mixture was sealed in a bomb and heated at 70°–80° C. for 24 hours. The bomb was cooled, opened and the solution taken to near dryness. A 20 ml portion of chloroform was added followed by 20 ml of methanol, 2 ml of water and 700 mg of silver carbonate. The mixture was stirred for 2 hours then filtered through diatomaceous earth. The solvents were removed with the exception of dimethylformamide and the remainder was evaporated from toluene, again with the exception of dimethylformamide. To the cooled remainder was added 50 ml of trimethylamine. The solution was again sealed in a bomb, heated at 80° C. for 30 hours, then allowed to stand at room temperature for 72 hours. The bomb was opened, the solution evaporated, 20 ml of chloroform, 20 ml of methanol, 2 ml of water and 700 mg of silver carbonate were added, the mixture stirred for 2 hours, filtered through diatomaceous earth and taken to dryness. A 250 ml column was prepared and charged with silica gel in 10% methanol in chloroform. The column was washed with 300 ml of the same solvent system, then the above residue was dissolved in the same solvent system and applied to the column. The column was eluted in succession with 500 ml of 10% methanol in chloroform, 500 ml of 20% methanol in chloroform, then 750 ml of 30% methanol in chloroform to remove the mobiles, then eluted with chloroform:methanol:water (65:35:6) to elute the product. The product fractions were combined and evaporated, giving 1.0 g of the desired compound as a glass.

EXAMPLE 33

2-[[[3-[[5-(Dodecyloxy)-1-naphthalenyl]oxy]-2-hydroxypropoxy]hydroxyphosphinyl]oxy]-N,N,N-trimethylethanaminium, hydroxide, inner salt A mixture of 2.6 g of 7-[[[5-(dodecyloxy)-1-naphthalenyl]oxy]methyl]-4-hydroxy-N,N,N-trimethyl-9-phenyl-3,5,8-trioxa-4-phosphanonan-1-aminium, 4-oxide, hydroxide, inner salt, 0.5 g of 5% palladium on carbon, 20 ml of glacial acetic acid and 20 ml of methanol was shaken in a Parr apparatus for 5 hours. The mixture was filtered, the solvent removed, ether added and the resulting solid collected, giving 2.06 g of the desired compound as a white powder, mp 45° C.

EXAMPLE 34

2-[[[3-[3-(Dodecyloxy)-2-methylphenoxy]-2-hydroxypropoxy]-hydroxyphosphinyl]oxy]-N,N,N-trimethylethanaminium, hydroxide, inner salt A mixture of 6.0 g of 3-[[3-(dodecyloxy)-2-methylphenoxy]methyl]-6-hydroxy-N,N,N-trimethyl-1-phenyl-2,5,7-trioxa-6-phosphanonan-9-aminium, 6-oxide, hydroxide, inner salt, 1.3 g of 5% palladium on carbon catalyst, 50 ml of glacial acetic acid and 50 ml of methanol was shaken in a Parr apparatus for 1.5 hours, then filtered through diatomaceous earth. The solvent was removed, toluene added and removed and the residue stirred with ether. The resulting solid was collected, giving 5.0 g of the desired compound, mp 97°–101° C.

EXAMPLE 35

2-[[[3-[[7-(Dodecyloxy)-2-naphthalenyl]oxy]-2-hydroxypropoxy]hydroxyphosphinyl]oxy]-N,N,N-trimethylethanaminium, hydroxide, inner salt A mixture of 3.96 g of 3-[[[7-(dodecyloxy)-2-naphthalenyl]oxy]methyl]-6-hydroxy-N,N,N-trimethyl-1-phenyl-2,5,7-trioxa-6-phosphanonan-9-aminium, 6-oxide, hydroxide, inner salt, 0.9 g of 5% palladium on carbon catalyst, 35 ml of glacial acetic acid and 35 ml of methanol was shaken in a Parr apparatus for 3 hours and then filtered. The solvent was removed and the residue treated with ether, giving 3.0 g of the desired compound as a white solid.

EXAMPLE 36

2-[[[3-[[4-(Dodecyloxy)-1-naphthalenyl]oxy]-2-hydroxypropoxy]hydroxyphosphinyl]oxy]-N,N,N-trimethylethanaminium, hydroxide, inner salt A mixture of 5.0 g of 3-[[[4-(dodecyloxy)-1-naphthalenyl]oxy]methyl]-6-hydroxy-N,N,N-trimethyl-1-phenyl-2,5,7-trioxa-6-phosphanonan-9-aminium, 6-oxide, hydroxide, inner salt, 1.1 g of 5% palladium on carbon catalyst, 45 ml of glacial acetic acid and 45 ml of methanol was shaken in a Parr apparatus for 4 hours, then filtered and the solvent removed. Toluene was added and removed, then ether was added and the solid collected, giving 3.5 g of the desired compound as a white sticky solid.

EXAMPLE 37

2-[[[3-[[6-(Dodecyloxy)-2-naphthalenyl]oxy]-2-hydroxypropoxy]hydroxyphosphinyl]oxy]-N,N,N-trimethylethanaminium, hydroxide, inner salt A mixture of 4.4 g of 3-[[[5-(dodecyloxy)-1-naphthalenyl]oxy]methyl]-6-hydroxy-N,N,N-trimethyl-1-phenyl-2,5,7-trioxa-6-phosphanonan-9-aminium, 6-oxide, hydroxide, inner salt, 1.1 g of 5% palladium on carbon, 45 ml of glacial acetic acid and 45 ml of methanol was shaken on a Parr apparatus for 5 hours, then filtered. The solvent was removed and ether was added, giving 3.3 g of the desired compound as a white solid.

EXAMPLE 38

2-[[[3-[2,4-Bis(1,1-dimethylethyl)-5-(dodecyloxy)-phenoxy]-2-hydroxypropoxy]hydroxyphosphinyl]oxy]-N,N,N-trimethylethanaminium, hydroxide, inner salt A mixture of 4.0 g of 3-[[2,4-bis(1,1-dimethylethyl)-5-(dodecyloxy)phenoxy]methyl]-6-hydroxy-N,N,N-trimethyl-1-phenyl-2,5,7-trioxa-6-phosphanonan-9-aminium, 6-oxide, hydroxide, inner salt, 1.0 g of 5% palladium on carbon, 45 ml of glacial acetic acid and 45 ml of methanol was shaken in a Parr apparatus for 3 hours, then filtered. The solvent was removed, giving 3.49 g of the desired compound as a thick oil.

EXAMPLE 39

1-[[[3-[5-(Dodecyloxy)-1-naphthalenyloxy]-2-hydroxypropoxy]hydroxyphosphinyl]oxy]-N,N,N-trimethyl-2-propanaminium, hydroxide, inner salt A solution of 940 mg of 3-[[[5-(dodecyloxy)-1-naphthalenyl]oxy]methyl]-6-hydroxy-N,N,N-trimethyl-1-phenyl-2,5,7-trioxa-6-phosphadecan-9-aminium, 6-oxide, hydroxide, inner salt in 25 ml of glacial acetic acid and 25 ml of methanol was hydrogenated with 0.5 g of 5% palladium on carbon in a Parr apparatus overnight. The mixture was filtered, taken to dryness and evaporated twice with toluene. The residue was triturated with ether, giving 662 mg of the desired compound as a waxy solid.

EXAMPLE 40

7-[[[5-(Dodecyloxy)-1-naphthalenyl]oxy]methyl]-4-hydroxy-N,N,N-trimethyl-9-oxo-3,5,8-trioxa-4-phosphadecan-1-aminium, 4-oxide, hydroxide, inner salt A mixture of 1.5 g of 2-[[[3-[[5-(dodecyloxy)-1-naphthalenyl]oxy]-2-hydroxypropoxy]hydroxyphosphinyl]oxy]-N,N,N-trimethylethanaminium, hydroxide, inner salt, 6.74 g of acetic anhydride and 2.67 g of triethylamine in 75 ml of chloroform was refluxed for 4.5 hours. The solvent and excess anhydride were removed at reduced pressure. The residue was stirred in ether, giving 1.25 g of the desired product, mp 45° C.

EXAMPLE 41

7-[[3-(Dodecyloxy)-2-methylphenoxy]methyl]-4-hydroxy-N,N,N-trimethyl-9-oxo-3,5,8-trioxa-4-phosphadecan-1-aminium, 4-oxide, hydroxide, inner salt A mixture of 3.0 g of 2-[[[3-[3-(dodecyloxy)-2-methylphenoxy]-2-hydroxypropoxy]hydroxyphosphinyl]oxy]-N,N,N-trimethylethanaminium, hydroxide, inner salt, 14.4 g of acetic anhydride and 5.71 g of triethylamine in 200 ml of chloroform was refluxed for 4 hours. The solvent and excess anhydride were removed. Toluene was added and removed, giving 3.1 g of the desired product as an oil.

EXAMPLE 42

7-[[[7-(Dodecyloxy)-2-naphthalenyl]oxy]methyl]-4-hydroxy-N,N,N-trimethyl-9-oxo-3,5,8-trioxa-4-phosphadecan-1-aminium, 4-oxide, hydroxide, inner salt A mixture of 2.5 g of 2-[[[3-[[7-(dodecyloxy)-2-naphthalenyl]oxy]-2-hydroxypropoxy]hydroxyphosphinyl]oxy]-N,N,N-trimethylethanaminium, hydroxide, inner salt, 11.24 g of acetic anhydride and 4.46 g of triethylamine in 160 ml of chloroform was refluxed for 4 hours. The solvent was removed, toluene was added and removed twice, then ether was added. The very hygroscopic solid-oil was collected, giving the desired product.

EXAMPLE 43

7-[[[4-(Dodecyloxy)-1-naphthalenyl]oxy]methyl]-4-hydroxy-N,N,N-trimethyl-9-oxo-3,5,8-trioxa-4-phosphadecan-1-aminium, 4-oxide, hydroxide, inner salt A mixture of 2.75 g of 2-[[[3-[[4-(dodecyloxy)-1-naphthalenyl]oxy]-2-hydroxypropoxy]hydroxyphosphinyl]- oxy]-N,N,N-trimethylethanaminium, hydroxide, inner salt, 12.36 g of acetic anhydride and 4.9 g of triethylamine in 170 ml of chloroform was refluxed for 4 hours. The excess anhydride and solvent were removed at reduced pressure. Toluene was added and removed several times. Ether was added and the resulting solid collected and dried in vacuo, giving the desired product as a gum.

EXAMPLE 44

7-[[[6-(Dodecyloxy)-2-naphthalenyl]oxy]methyl]-4-hydroxy-N,N,N-trimethyl-9-oxo-3,5,8-trioxa-4-phosphadecan-1-aminium, 4-oxide, hydroxide, inner salt A mixture of 2.7 g of 2-[[[3-[[6-(dodecyloxy)-2-naphthalenyl]oxy]-2-hydroxypropoxy]hydroxyphosphinyl]oxy]-N,N,N-trimethylethanaminium, hydroxide, inner salt, 12.14 g of acetic anhydride and 4.81 g of triethylamine in 170 ml of chloroform was refluxed for 4.5 hours. The solvent and excess anhydride were removed, toluene was added and removed, then ether was added. The resulting sticky solid was collected, giving 2.4 g of the desired product.

EXAMPLE 45

7-[[2,4-Bis(1,1-dimethylethyl)-5-(dodecyloxy)phenoxy]methyl]-4-hydroxy-N,N,N-trimethyl-9-oxo-3,5,8-trioxa-4-phosphadecan-1-aminium, 4-oxide, hydroxide, inner salt A mixture of 2.5 g of 2-[[[3-[2,4-bis(1,1-dimethylethyl)-5-(dodecyloxy)phenoxy]-2-hydroxypropoxy]hydroxyphosphinyl]oxy]-N,N,N-trimethylethanaminium, hydroxide, inner salt, 10.13 g of acetic anhydride and 4.02 g of triethylamine in 170 ml of chloroform was refluxed for 4 hours. The solvent and excess anhydride were removed and the residue dried in vacuo, giving 2.6 g of the desired product as an oil.

EXAMPLE 46

4-[[[5-(Dodecyloxy)-1-naphthalenyl]oxy]methyl]-7-hydroxy-N,N,N-trimethyl-2-oxo-3,6,8-trioxa-7-phosphaundecan-10-aminium, 7-oxide, hydroxide, inner salt A mixture of 600 mg of 1-[[[3-[5-(dodecyloxy)-1-naphthalenyloxy]-2-hydroxypropoxy]hydroxyphosphinyl]oxy]-N,N,N-trimethyl-2-propanaminium, hydroxide, inner salt in 30 ml of dry chloroform containing 2.63 g of acetic anhydride and 1.04 g of triethylamine was stirred at reflux for 5 hours, then taken to dryness. The residue was evaporated twice with toluene then chromatographed on a silica gel column. The residue was applied in 20% methanol in chloroform. The column was eluted with 250 ml of 20% chloroform in methanol, then 250 ml of 30% methanol in chloroform to remove mobile impurities. The product was eluted with chloroform:methanol:water (60:35:6). The 50 ml product fractions were combined, evaporated and dried in vacuo, giving 278 mg of the desired product.

The preparation of the compounds of this invention wherein $R_3$ is a benzyloxy group is described hereinbelow in Examples 47-54.

EXAMPLE 47

2,2-Dimethyl-4-[[4-(phenylmethoxy)phenoxy]methyl]-1,3-dioxolane

To a suspension of 18 g of washed (hexane) 50% sodium hydride in dimethylformamide was added dropwise a solution of 50.06 g of p-(benzyloxy)phenol in dimethylformamide. The mixture was stirred for ½ hour, then a solution of 63 g of the mesylate of solketal in dimethylformamide was added. After one hour the mixture was poured onto ice and extracted several times with ether. The ether extracts were combined, washed with water, dried and the solvents evaporated. The crude compound was recrystallized from ether-hexane, giving 21 g of the desired compound, mp 87°–89° C.

EXAMPLE 48

3-[4-(Phenylmethoxy)phenoxy]-1,2-propanediol

A mixture of 8.98 g of 2,2-dimethyl-4-[[4-(phenylmethoxy)phenoxy]methyl]-1,3-dioxolane, 15 g of a strongly acidic ion exchange resin and 200 ml of water was refluxed for 24 hours, then allowed to cool and methylene chloride was added. The mixture was filtered and the organic layer separated and saved. The aqueous layer was extracted several times with methylene chloride. All organic solutions were combined, dried and evaporated, giving 3.0 g of the desired compound, mp 125°–127° C.

EXAMPLE 49

1-[(4-Methoxyphenyl)diphenylmethoxy]-3-[4-(phenylmethoxy)-phenoxy]-2-propanol

To a solution of 18.9 g of 3-[4-(phenylmethoxy)phenoxy]-1,2-propanediol in 50 ml of pyridine and 24 ml of tetrahydrofuran was added 25.57 g of methoxy trityl chloride in several portions. This mixture was stirred for 24 hours and the solvents removed under reduced pressure. The residue was dissolved in chloroform, washed with aqueous sodium bicarbonate, then water, dried and evaporated, giving 30 g of the desired compound.

EXAMPLE 50

1-[(4-Methoxyphenyl)diphenylmethoxy]-3-[4-(phenylmethoxy)-phenoxy]-2-propanol, acetate A mixture of 18.6 g of 1-[(4-methoxyphenyl)diphenylmethoxy]-3-[4-(phenylmethoxy)phenox]-2-propanol, 20 ml of acetic anhydride and 60 ml of pyridine was stirred under argon for 24 hours, then poured onto ice and extracted several times with chloroform. The chloroform extracts were combined, washed with aqueous sodium bicarbonate, then water, dried and the solvents removed under reduced pressure. The residue was coevaporated with toluene, giving 20.4 g of the desired compound.

EXAMPLE 51

3-[4-(Phenylmethoxy)phenyl]-1,2-propanediol, 2-acetate

A 17.64 g portion of 1-[(4-methoxyphenyl)diphenylmethoxy]-3-[4-(phenylmethoxy)phenoxy]-2-propanol, acetate was packed into a boric acid-silicic acid column using 3 liters of petroleum ether as eluent. After all the methoxy trityl carbinol was eluted, the column was eluted with petroleum ether:ether (9:1), then petroleum ether:ether (7:3). The product was isolated and crystallized using hexane:ether.

EXAMPLE 52

2-(Acetyloxy)-3-[4-(phenylmethoxy)phenoxy]propyl phosphoric acid, 2-bromoethyl ester To a solution of 727 mg of 3-[4-(phenylmethoxy)phenyl]-1,2-propanediol, 2-acetate in 20 ml of carbon tetrachloride (warmed to 40° C.) was added a solution of 662 mg of 2-bromoethyl phosphorodichlorodate in carbon tetrachloride followed by 279 mg of triethylamine. The mixture was stirred under argon for 3 hours, the filtered through diatomaceous earth. The filtrate was concentrated and the residue dissolved in 15 ml of tetrahydrofuran. A 15 ml portion of 0.5 M aqueous sodium acetate was added, the mixture was stirred one hour, brine was added and the mixture extracted with three 70 ml portions of ethyl acetate. The organic extracts were combined, dried and the solvent evaporated. The residue was purified by chromatography on magnesium silicate eluting first with chloroform, then with chloroform:methanol (9:1) and finally eluting the product with chloroform:methanol (9:2), giving 540 mg of the desired compound, mp 60° C.

EXAMPLE 53

4-Hydroxy-N,N,N-trimethyl-9-oxo-7-[[4-(phenylmethoxy)-phenoxy]methyl]-3,5,8-trioxa-4-phosphadecan-1-aminium, 4-oxide, hydroxide, inner salt A mixture of 300 mg of 2-(acetyloxy)-3-[4-(phenylmethoxy)phenoxy]propyl phosphoric acid, 2-bromoethyl ester in 15 ml of a solution of 33% trimethylamine in acetonitrile was heated to reflux for 16 hours. The solvent was removed under reduced pressure and the crude compound purified by chromatography on silica gel, eluting first with chloroform, then chloroform:methanol (9:1), then chloroform:methanol:water (65:25:1) and finally eluting the product with methanol, giving 185 mg of the desired compound.

EXAMPLE 54

2-(Acetyloxy)-3-[4-(phenylmethoxy)phenoxy]propyl phosphoric acid 2-bromopropyl ester A mixture of 822 mg of 4-hydroxy-N,N,N-trimethyl-9-oxo-7-[[4-(phenylmethoxy)phenoxy]methyl]-3,5,8-trioxa-4-phosphadecan-1-aminium, 4-oxide, hydroxide, inner salt, 930 mg of 2-bromopropyl phosphorodichlorodate and 384 mg of triethylamine in 8 ml of carbon tetrachloride was stirred for 2 hours, filtered through diatomaceous earth and the solvent removed. The residue was dissolved in 10 ml of tetrahydrofuran, 10 ml of 0.5 M aqueous sodium acetate was added and the mixture was stirred for one hour. The tetrahydrofuran was removed and the remainder extracted several times with ethyl acetate. The extracts were combined, washed with brine, dried and the solvents evaporated. The crude product was purified by chromatography on magnesium silicate, eluting first with chloroform and then eluting the product with chloroform:methanol (10:1), giving 1.1 g of the desired compound.

TABLE III

| Alkyl Amines |
|---|
| trimethyl amine |
| dimethyl amine |
| methyl amine |
| triethyl amine |
| diethyl amine |
| ethyl amine |
| tripropyl amine |
| dipropyl amine |
| propyl amine |
| pyrrolidine |
| N—methyl pyrrolidine |
| butyl amine |
| ammonia |

What is claimed is:

1. A method of treating hypertension in a warm-blooded animal comprising administering to said animal an effective amount of a compound, including the individual R and S enantiomers and racemic mixture, represented by the formula:

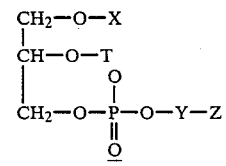

wherein X is selected from the group consisting of a phenyl radical substituted at any position with a $C_1$-$C_{20}$ branched or straight chain alkoxy or benzyloxy, alone, or further substituted at any other positions with one or more groups consisting of $C_1$-$C_{15}$ branched or straight chain alkyl, $C_1$-$C_{15}$ branched or straight chain alkoxy and halogen, and a naphthalene radical substituted at any position with a $C_1$-$C_{20}$ branched or straight chain alkoxy or benzyloxy, alone, or further substituted at any other positions with one or more groups consisting of $C_1$-$C_{15}$ branched or straight chain alkyl, $C_1$-$C_{15}$ branched or straight chain alkoxy and halogen; T is selected from the group consisting of hydrogen and

wherein $R_1$ is selected from the group consisting of hydrogen, $C_1$-$C_4$ branched or straight chain alkyl, $C_1$-$C_4$ branched or straight chain alkoxy and $C_1$-$C_4$ branched or straight chain alkylamino; Y is selected from the group of bivalent radicals consisting of —$(CH_2)_p$—and—$(CHR)_p$—, wherein p is an integer from 2 to 10 and the moiety —$(CHR)_p$—represents an alkylene chain substituted with one or more $C_1$-$C_8$ alkyl groups or phenyl groups; Z is selected from the group consisting of

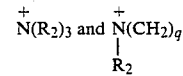

wherein q is an integer from 4–7 and $R_2$ may be the same or different and is selected from the group consisting of hydrogen and $C_1$-$C_4$ branched or straight chain alkyl.

2. A pharmaceutical composition of matter in dosage unit form comprising a compound, including the individual R and S enantiomers and racemic mixture, represented by the formula:

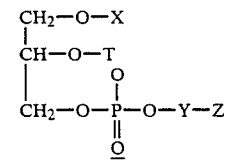

wherein X is selected from the group consisting of a phenyl radical substituted at any position with a $C_1$-$C_{20}$ branched or straight chain alkoxy or benzyloxy, alone, or further substituted at any other positions with one or more groups consisting of $C_1$-$C_{15}$ branched or straight chain alkyl, $C_1$-$C_{15}$ branched or straight chain alkoxy and halogen, and a naphthalene radical substituted at any position with a $C_1$-$C_{20}$ branched or straight chain alkoxy or benzyloxy, alone, or further substituted at any other positions with one or more groups consisting of $C_1$-$C_{15}$ branched or straight chain alkyl, $C_1$-$C_{15}$ branched or straight chain alkoxy and halogen; T is selected from the group consisting of hydrogen and

wherein $R_1$ is selected from the group consisting of hydrogen, $C_1$-$C_4$ branched or straight chain alkyl, $C_1$-$C_4$ branched or straight chain alkoxy and $C_1$-$C_4$ branched or straight chain alkylamino; Y is selected from the group of bivalent radicals consisting of —$(CH_2)_p$—and—$(CHR)_p$—, wherein p is an integer from 2 to 10 and the moiety —$(CHR)_p$—represents an alkylene chain substituted with one or more $C_1$-$C_8$ alkyl groups or phenyl groups; Z is selected from the group consisting of

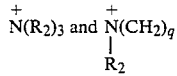

wherein q is an integer from 4–7 and $R_2$ may be the same or different and is selected from the group consisting of hydrogen and $C_1$-$C_4$ branched or straight chain alkyl in association with a pharmaceutically acceptable carrier.

3. A method of treating hypertension in a warm-blooded animal comprising administering to said animal an effective amount of a compound, including the individual R and S enantiomers and racemic mixture represented by the formula:

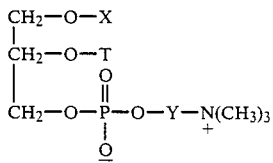

wherein X is selected from a phenyl radical substituted at any position with a $C_{12}$ alkoxy or benzyloxy and optionally substituted at any other positions with one or more groups consisting of $C_1$-$C_4$ alkyl and a naphthalene radical substituted at any position with a $C_{12}$ alkoxy; T is hydrogen or acetyl; and Y is ethyl or isopropyl.

4. A pharmaceutical composition of matter in dosage unit form comprising a compound, including the individual R and S enantiomers and racemic mixture, in association with a pharmaceutically acceptable carrier, wherein said compound is of the formula:

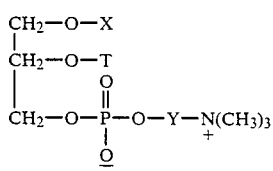

wherein X is selected from a phenyl radical substituted at any position with a $C_{12}$ alkoxy or benzyloxy, alone, or further substituted at any other positions with one or more groups consisting of $C_1$-$C_4$ alkyl and a naphthalene radical substituted at any position with a $C_{12}$ alkoxy; T is hydrogen or acetyl; and Y is ethyl or isopropyl.

5. Compounds, including the individual R and S enantiomers and the racemic mixtures represented by the formula:

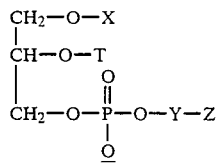

wherein X is selected from the group consisting of a phenyl radical substituted at any position with a $C_1$-$C_{20}$ branched or straight chain alkoxy or benzyloxy, alone, or further substituted at any other positions with one or more groups consisting of $C_1$-$C_{15}$ branched or straight chain alkyl, $C_1$-$C_{15}$ branched or straight chain alkoxy and halogen, and a naphthalene radical substituted at any position with a $C_1$-$C_{20}$ branched or straight chain alkoxy or benzyloxy, alone, or further substituted at any other positions with one or more groups consisting of $C_1$-$C_{15}$ branched or straight chain alkyl, $C_1$-$C_{15}$ branched or straight chain alkoxy and halogen; T is selected from the group consisting of hydrogen and

wherein $R_1$ is selected from the group consisting of hydrogen, $C_1$-$C_4$ branched or straight chain alkyl, $C_1$-$C_4$ branched or straight chain alkoxy and $C_1$-$C_4$ branched or straight chain alkylamino; Y is selected from the group of bivalent radicals consisting of —$(CH_2)_p$—and—$(CHR)_p$—, wherein p is an integer from 2 to 10 and the moiety —$(CHR)_p$—represents an alkylene chain substituted with one or more $C_1$-$C_8$ alkyl groups or phenyl groups; Z is selected from the group consisting of

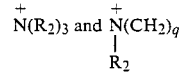

wherein q is an integer from 4–7 and $R_2$ may be the same or different and is selected from the group consisting of hydrogen and $C_1$-$C_4$ branched or straight chain alkyl.

6. The compounds according to claim 5, wherein

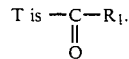

7. The compounds according to claim 6, wherein Z is —$N^t(CH_3)_3$.

8. The compounds according to claim 7, wherein Y is —$(CH_2)_p$—.

9. The compounds according to claim 8, wherein T is

and p is 2.

10. The compound, including the individual R and S enantiomers and the racemic mixture represented by the formula:

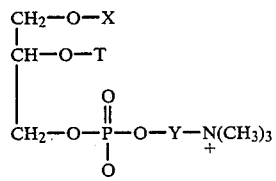

wherein X is a phenyl radical substituted at any position with a $C_{12}$ alkoxy or benzyloxy, alone or further substituted at any other positions with one or more groups consisting of $C_1$–$C_4$ alkyl; T is hydrogen or acetyl; and Y is ethyl or isopropyl.

11. The compound including the individual R and S enantiomers and the racemic mixture represented by the formula:

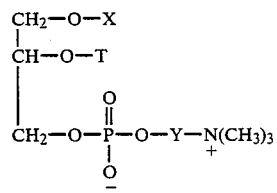

wherein X is a naphthalene radical substituted at any position with a $C_{12}$ alkoxy; T is hydrogen or acetyl; and Y is ethyl or isopropyl.

12. The compound 7-[[3-(dodecyloxy)-2-methylphenoxy]methyl]-4-hydroxy-N,N,N-trimethyl-9-oxo-3,5,8-trioxa-4-phosphadecan-1-aminium, 4-oxide, hydroxide, inner salt.

13. The compound 7-[[3-(dodecyloxy)-4,6-(di-t-butyl)phenoxy]methyl]-4-hydroxy-N,N,N-trimethyl-9-oxo-3,5,8-trioxa-4-phosphadecan-1-aminium, 4-oxide, hydroxide, inner salt.

14. Compounds, including the individual R and S enantiomers and racemic mixture mixture represented by the formula:

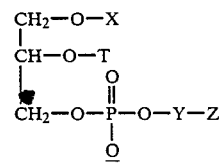

wherein X is selected from phenyl radical substituted at any position with a $C_8$–$C_{12}$ alkoxy or benzyloxy, alone, or further substituted at any other positions with one or more groups consisting of $C_1$–$C_4$ alkyl and a naphthalene radical substituted at any position with a $C_8$–$C_{12}$ alkoxy; T is hydrogen or

wherein $R_1$ is selected from hydrogen and $C_1$–$C_4$ alkyl; Y is a bivalent radical selected from $-(CH_2)_p-$, wherein p is an integer from 2 to 5, or $(CHR^1)_p$, wherein p is defined as above and $R^1$ is methyl or phenyl; and Z is selected from

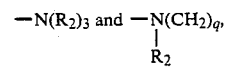

wherein $R_2$ may be the same or different and is selected from hydrogen and $C_1$–$C_4$ alkyl and q is an integer from 4 to 7.

* * * * *